United States Patent
Saint et al.

(10) Patent No.: US 7,637,868 B2
(45) Date of Patent: Dec. 29, 2009

(54) COMPOSITE MATERIAL FOR IMPLANTABLE DEVICE

(75) Inventors: Sean Saint, San Diego, CA (US); Mark Brister, Encinitas, CA (US)

(73) Assignee: DexCom, Inc., San Diego, CA (US)

( * ) Notice: Subject to any disclaimer, the term of this patent is extended or adjusted under 35 U.S.C. 154(b) by 684 days.

(21) Appl. No.: 11/034,343

(22) Filed: Jan. 11, 2005

(65) Prior Publication Data
US 2005/0181012 A1   Aug. 18, 2005

Related U.S. Application Data

(60) Provisional application No. 60/535,885, filed on Jan. 12, 2004, provisional application No. 60/535,914, filed on Jan. 12, 2004.

(51) Int. Cl.
*A61B 1/00* (2006.01)
(52) U.S. Cl. ............... 600/365; 600/300; 607/36
(58) Field of Classification Search ......... 600/300, 600/309–316, 345–365; 607/36
See application file for complete search history.

(56) References Cited

U.S. PATENT DOCUMENTS

| | | | |
|---|---|---|---|
| 2,402,306 | A | 6/1946 | Turkel |
| 3,219,533 | A | 11/1965 | Mullins |
| 3,381,371 | A | 5/1968 | Russell |
| 3,775,182 | A | 11/1973 | Patton et al. |
| 3,933,593 | A | 1/1976 | Sternberg |
| 3,979,274 | A | 9/1976 | Newman |
| 4,197,840 | A | 4/1980 | Beck et al. |
| 4,240,889 | A | 12/1980 | Yoda et al. |

(Continued)

FOREIGN PATENT DOCUMENTS

EP   0 127 958   12/1984

(Continued)

OTHER PUBLICATIONS

Beach, et al. 1999. Subminiature implantable potentiostat and modified commercial telemetry device for remote glucose monitoring. *IEEE Transactions on Instrumentation and Measurement*, 48(6):1239-1245.

(Continued)

*Primary Examiner*—Scott M Getzow
(74) *Attorney, Agent, or Firm*—Knobbe Martens Olson & Bear LLP

(57) ABSTRACT

Devices suitable for implantation in a body of a host and systems and methods for their manufacture are provided. The implantable devices include a composite material formed at least from a matrix material and hollow gas-filled beads. In preferred embodiments, the composite material includes a polymeric matrix mixed with hollow air-filled glass beads, which are mixed and cured to form at least a portion of the body of the implantable device. Implantable devices including this composite material have decreased weight and/or overall density as compared to implantable devices without the beads incorporated therein, which is believed to improve the acceptance and function of the implantable device in vivo. Additionally, implantable devices concerned with transmitting and receiving via RF are believed to achieve improved RF performance due to a reduced dielectric constant provided by the incorporation of beads within the composite material.

26 Claims, 3 Drawing Sheets

U.S. PATENT DOCUMENTS

| | | | |
|---|---|---|---|
| 4,255,500 A | 3/1981 | Hooke |
| 4,324,257 A | 4/1982 | Albarda et al. |
| 4,374,013 A | 2/1983 | Enfors |
| 4,418,148 A | 11/1983 | Oberhardt |
| 4,431,507 A | 2/1984 | Nankai et al. |
| 4,571,292 A | 2/1986 | Liu et al. |
| RE32,361 E | 2/1987 | Duggan |
| 4,663,824 A | 5/1987 | Kenmochi |
| 4,721,677 A | 1/1988 | Clark, Jr. |
| 4,750,496 A | 6/1988 | Reinhart et al. |
| 4,849,458 A | 7/1989 | Reed et al. |
| 4,871,440 A | 10/1989 | Nagata et al. |
| 4,927,407 A | 5/1990 | Dorman |
| 4,927,516 A | 5/1990 | Yamaguchi et al. |
| 4,953,552 A | 9/1990 | DeMarzo |
| 4,955,861 A | 9/1990 | Enegren et al. |
| 4,974,929 A | 12/1990 | Curry |
| 4,992,794 A | 2/1991 | Brouwers |
| 5,034,112 A | 7/1991 | Murase et al. |
| 5,097,834 A | 3/1992 | Skrabal |
| 5,165,407 A | 11/1992 | Wilson et al. |
| 5,171,689 A | 12/1992 | Kawaguri et al. |
| 5,190,041 A | 3/1993 | Palti |
| 5,249,576 A | 10/1993 | Goldberger et al. |
| 5,282,848 A | 2/1994 | Schmitt |
| 5,299,571 A | 4/1994 | Mastrototaro |
| 5,307,263 A | 4/1994 | Brown |
| 5,312,361 A | 5/1994 | Zadini et al. |
| 5,322,063 A | 6/1994 | Allen et al. |
| 5,337,747 A | 8/1994 | Neftel |
| 5,352,351 A | 10/1994 | White |
| 5,372,133 A | 12/1994 | Hogen Esch |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,411,647 A | 5/1995 | Johnson et al. |
| 5,431,160 A | 7/1995 | Wilkins |
| 5,462,645 A | 10/1995 | Albery et al. |
| 5,469,846 A | 11/1995 | Khan |
| 5,482,008 A | 1/1996 | Stafford et al. |
| 5,482,473 A | 1/1996 | Lord et al. |
| 5,497,772 A | 3/1996 | Schulman et al. |
| 5,564,439 A | 10/1996 | Picha |
| 5,568,806 A | 10/1996 | Cheney, II et al. |
| 5,569,186 A | 10/1996 | Lord et al. |
| 5,569,462 A | 10/1996 | Martinson et al. |
| 5,571,395 A | 11/1996 | Park et al. |
| 5,575,930 A | 11/1996 | Tietje-Girault et al. |
| 5,582,184 A | 12/1996 | Ericson et al. |
| 5,607,565 A | 3/1997 | Azarnia et al. |
| 5,611,900 A | 3/1997 | Worden |
| 5,628,890 A | 5/1997 | Carter et al. |
| 5,640,954 A | 6/1997 | Pfeiffer |
| 5,686,829 A | 11/1997 | Girault |
| 5,704,354 A | 1/1998 | Priedel et al. |
| 5,706,807 A | 1/1998 | Picha |
| 5,707,502 A | 1/1998 | McCaffrey et al. |
| 5,711,861 A | 1/1998 | Ward et al. |
| 5,741,330 A | 4/1998 | Brauker et al. |
| 5,749,907 A | 5/1998 | Mann |
| 5,787,900 A | 8/1998 | Butler et al. |
| 5,791,344 A | 8/1998 | Schulman et al. |
| 5,800,420 A | 9/1998 | Gross |
| 5,814,599 A | 9/1998 | Mitragotri et al. |
| 5,833,603 A | 11/1998 | Kovacs et al. |
| 5,840,148 A | 11/1998 | Campbell et al. |
| 5,851,197 A | 12/1998 | Marano et al. |
| 5,861,019 A | 1/1999 | Sun et al. |
| 5,871,514 A | 2/1999 | Wiklund et al. |
| 5,879,373 A | 3/1999 | Roper et al. |
| 5,895,235 A | 4/1999 | Droz |
| 5,897,578 A | 4/1999 | Wiklund et al. |
| 5,913,998 A | 6/1999 | Butler et al. |
| 5,917,346 A | 6/1999 | Gord |
| 5,919,215 A | 7/1999 | Wiklund et al. |
| 5,928,130 A | 7/1999 | Schmidt |
| 5,954,643 A | 9/1999 | Van Antwerp et al. |
| 5,963,132 A | 10/1999 | Yoakum |
| 5,964,261 A | 10/1999 | Neuenfeldt et al. |
| 5,964,993 A | 10/1999 | Blubaugh et al. |
| 5,985,129 A | 11/1999 | Gough et al. |
| 5,989,409 A | 11/1999 | Kurnik et al. |
| 5,999,848 A | 12/1999 | Gord et al. |
| 6,001,067 A | 12/1999 | Shults et al. |
| 6,011,984 A | 1/2000 | Van Antwerp et al. |
| 6,013,113 A | 1/2000 | Mika |
| 6,016,448 A | 1/2000 | Busacker et al. |
| 6,049,727 A | 4/2000 | Crothall |
| 6,066,083 A | 5/2000 | Slater et al. |
| 6,066,448 A | 5/2000 | Wohlstadter et al. |
| 6,081,736 A | 6/2000 | Colvin et al. |
| 6,088,608 A | 7/2000 | Schulman et al. |
| 6,093,156 A | 7/2000 | Cunningham et al. |
| 6,093,172 A | 7/2000 | Funderburk et al. |
| 6,107,083 A | 8/2000 | Collins et al. |
| 6,115,634 A | 9/2000 | Donders et al. |
| 6,117,290 A | 9/2000 | Say |
| 6,119,028 A | 9/2000 | Schulman et al. |
| 6,122,536 A | 9/2000 | Sun et al. |
| 6,167,614 B1 | 1/2001 | Tuttle et al. |
| 6,175,752 B1 | 1/2001 | Say et al. |
| 6,201,980 B1 | 3/2001 | Darrow et al. |
| 6,201,993 B1 | 3/2001 | Kruse et al. |
| 6,208,894 B1 | 3/2001 | Schulman et al. |
| 6,212,416 B1 | 4/2001 | Ward et al. |
| 6,214,185 B1 | 4/2001 | Offenbacher et al. |
| 6,233,080 B1 | 5/2001 | Brenner et al. |
| 6,233,471 B1 | 5/2001 | Berner et al. |
| 6,248,067 B1 | 6/2001 | Causey, III et al. |
| 6,256,522 B1 | 7/2001 | Schultz |
| 6,259,937 B1 | 7/2001 | Schulman et al. |
| 6,264,825 B1 | 7/2001 | Blackburn et al. |
| 6,275,717 B1 | 8/2001 | Gross et al. |
| 6,284,478 B1 | 9/2001 | Heller et al. |
| 6,285,897 B1 | 9/2001 | Kilcoyne et al. |
| 6,293,925 B1 | 9/2001 | Safabash et al. |
| 6,300,002 B1 | 10/2001 | Webb et al. |
| 6,309,526 B1 | 10/2001 | Fujiwara et al. |
| 6,325,979 B1 | 12/2001 | Hahn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,360,888 B1 | 3/2002 | Melver et al. |
| 6,368,274 B1 | 4/2002 | Van Antwerp et al. |
| 6,372,244 B1 | 4/2002 | Antanavich et al. |
| 6,400,974 B1 | 6/2002 | Lesho |
| 6,406,066 B1 | 6/2002 | Uegane |
| 6,409,674 B1 | 6/2002 | Brockway et al. |
| 6,418,332 B1 | 7/2002 | Mastrototaro et al. |
| 6,424,847 B1 | 7/2002 | Mastrototaro et al. |
| 6,447,448 B1 | 9/2002 | Ishikawa et al. |
| 6,447,542 B1 | 9/2002 | Weadock |
| 6,454,710 B1 | 9/2002 | Ballerstadt et al. |
| 6,459,917 B1 | 10/2002 | Gowda et al. |
| 6,466,810 B1 | 10/2002 | Ward et al. |
| 6,477,395 B2 | 11/2002 | Schulman et al. |
| 6,484,046 B1 | 11/2002 | Say et al. |
| 6,498,043 B1 | 12/2002 | Schulman et al. |
| 6,498,941 B1 | 12/2002 | Jackson |
| 6,512,939 B1 | 1/2003 | Colvin et al. |
| 6,520,326 B2 | 2/2003 | McIvor et al. |
| 6,534,711 B1 | 3/2003 | Pollack |
| 6,541,107 B1 | 4/2003 | Zhong et al. |

| | | |
|---|---|---|
| 6,544,212 B2 | 4/2003 | Galley et al. |
| 6,546,268 B1 | 4/2003 | Ishikawa et al. |
| 6,547,839 B2 | 4/2003 | Zhang et al. |
| 6,558,320 B1 | 5/2003 | Causey |
| 6,560,471 B1 | 5/2003 | Heller et al. |
| 6,579,498 B1 | 6/2003 | Eglise |
| 6,585,763 B1 | 7/2003 | Keilman et al. |
| 6,589,229 B1 | 7/2003 | Connelly et al. |
| 6,605,072 B2 | 8/2003 | Struys et al. |
| 6,612,984 B1 | 9/2003 | Kerr |
| 6,654,625 B1 | 11/2003 | Say et al. |
| 6,673,596 B1 | 1/2004 | Sayler et al. |
| 6,699,383 B2 | 3/2004 | Lemire et al. |
| 6,702,857 B2 | 3/2004 | Brauker et al. |
| 6,721,587 B2 | 4/2004 | Gough |
| 6,730,200 B1 | 5/2004 | Stewart et al. |
| 6,731,976 B2 | 5/2004 | Penn et al. |
| 6,737,158 B1 * | 5/2004 | Thompson .............. 428/306.6 |
| 6,741,877 B1 | 5/2004 | Shults et al. |
| 6,773,565 B2 | 8/2004 | Kunimoto et al. |
| 6,793,802 B2 | 9/2004 | Lee et al. |
| 6,801,041 B2 | 10/2004 | Karinka et al. |
| 6,802,957 B2 | 10/2004 | Jung et al. |
| 6,809,507 B2 | 10/2004 | Morgan et al. |
| 6,809,653 B1 | 10/2004 | Mann et al. |
| 6,862,465 B2 | 3/2005 | Shults et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,965,791 B1 | 11/2005 | Hitchcock et al. |
| 7,025,743 B2 | 4/2006 | Mann et al. |
| 7,070,580 B2 | 7/2006 | Nielsen |
| 7,074,307 B2 | 7/2006 | Simpson et al. |
| 7,108,778 B2 | 9/2006 | Simpson et al. |
| 7,115,884 B1 * | 10/2006 | Walt et al. ................ 250/459.1 |
| 7,166,074 B2 | 1/2007 | Reghabit et al. |
| 7,207,974 B2 | 4/2007 | Safabash et al. |
| 7,267,665 B2 | 9/2007 | Steil et al. |
| 7,310,544 B2 | 12/2007 | Brister et al. |
| 2001/0041830 A1 | 11/2001 | Varalli et al. |
| 2002/0042561 A1 | 4/2002 | Schulman et al. |
| 2002/0099997 A1 | 7/2002 | Piret |
| 2003/0004457 A1 | 1/2003 | Andersson |
| 2003/0006669 A1 | 1/2003 | Pei et al. |
| 2003/0032874 A1 | 2/2003 | Rhodes et al. |
| 2003/0036773 A1 * | 2/2003 | Whitehurst et al. ............ 607/3 |
| 2003/0065254 A1 | 4/2003 | Schulman et al. |
| 2003/0078560 A1 | 4/2003 | Miller et al. |
| 2003/0097082 A1 | 5/2003 | Purdy et al. |
| 2003/0125613 A1 | 7/2003 | Enegren et al. |
| 2003/0130616 A1 | 7/2003 | Steil et al. |
| 2003/0187338 A1 | 10/2003 | Say et al. |
| 2003/0211625 A1 | 11/2003 | Cohan |
| 2003/0212346 A1 | 11/2003 | Yuzhakov et al. |
| 2003/0225437 A1 | 12/2003 | Ferguson |
| 2004/0045879 A1 | 3/2004 | Shults et al. |
| 2004/0074785 A1 | 4/2004 | Holker |
| 2004/0078219 A1 | 4/2004 | Kaylor |
| 2004/0106859 A1 | 6/2004 | Say et al. |
| 2004/0133164 A1 | 7/2004 | Funderburk et al. |
| 2004/0186365 A1 | 9/2004 | Jin et al. |
| 2004/0199059 A1 | 10/2004 | Brauker et al. |
| 2004/0236200 A1 | 11/2004 | Say et al. |
| 2004/0236251 A1 | 11/2004 | Roe et al. |
| 2004/0254433 A1 | 12/2004 | Bandis |
| 2005/0027180 A1 | 2/2005 | Goode et al. |
| 2005/0027181 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0112169 A1 | 5/2005 | Brauker et al. |
| 2005/0154271 A1 | 7/2005 | Rasdal et al. |
| 2005/0192557 A1 | 9/2005 | Brauker et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0258037 A1 | 11/2005 | Hajizadeh et al. |
| 2006/0015020 A1 | 1/2006 | Neale et al. |
| 2006/0189856 A1 * | 8/2006 | Petisce et al. ............... 600/309 |
| 2006/0200022 A1 | 9/2006 | Brauker et al. |
| 2006/0211921 A1 | 9/2006 | Brauker et al. |
| 2006/0222566 A1 | 10/2006 | Brauker et al. |
| 2006/0224108 A1 | 10/2006 | Brauker et al. |
| 2007/0027384 A1 | 2/2007 | Brister et al. |
| 2007/0027385 A1 | 2/2007 | Brister et al. |
| 2007/0032717 A1 | 2/2007 | Brister et al. |
| 2007/0032718 A1 | 2/2007 | Shults et al. |
| 2007/0093704 A1 | 4/2007 | Brister et al. |
| 2007/0203966 A1 | 8/2007 | Brauker et al. |
| 2007/0208244 A1 | 9/2007 | Brauker et al. |
| 2007/0213611 A1 | 9/2007 | Simpson et al. |
| 2007/0235331 A1 | 10/2007 | Simpson et al. |

FOREIGN PATENT DOCUMENTS

| | | |
|---|---|---|
| EP | 0 320 109 | 6/1989 |
| EP | 0 353 328 | 2/1990 |
| EP | 0 396 788 | 11/1990 |
| EP | 0 534 074 | 3/1993 |
| EP | 0 539 625 | 5/1993 |
| EP | 0 838 230 A | 4/1998 |
| EP | 0 967 788 | 12/1999 |
| FR | 2656423 | 6/1991 |
| FR | 2760962 | 9/1998 |
| JP | 62083849 | 4/1987 |
| JP | 2002-189015 | 7/2002 |
| WO | WO 92/07525 | 5/1992 |
| WO | WO 92/13271 | 8/1992 |
| WO | WO 94/22367 | 10/1994 |
| WO | WO 96/25089 | 2/1995 |
| WO | WO 95/07109 | 3/1995 |
| WO | WO 98/24358 | 6/1998 |
| WO | WO 00/13003 | 3/2000 |
| WO | WO 00/19887 | 4/2000 |
| WO | WO 00/32098 | 6/2000 |
| WO | WO 00/33065 | 6/2000 |
| WO | WO 00/59373 | 10/2000 |
| WO | WO 01/34243 A1 | 5/2001 |

OTHER PUBLICATIONS

Bowman, L.; Meindl, J. D. The packaging of implantable integrated sensors. IEEE Trans Biomed Eng 1986, 33, 248-255.

Cai, Q.; Zeng, K.; Ruan, C.; Desai, T. A.; Grimes, C. A. A wireless, remote query glucose biosensor based on a pH-sensitive polymer. Anal Chem 2004, 76, 4038-4043.

D'Arrigo, et al. Poro -Si based bioreactors for glucose monitoring and drugs production. Proc. of SPIE 2003, 4982, 178-184.

El-Sa'ad, L.; Yates, D. Moisture Absorption by Epoxy Resins: the Reverse Thermal Effect. Journal of Materials Science 1990, 25, 3577-3582.

Garg, S.; Schwartz, S.; Edelman, S. Improved Glucose Excursions Using an Implantable Real-Time Continuous Glucose Sensor in Adults with Type I Diabetes. Diabetes Care 2004, 27, 734-738.

Gilligan, et al. 1994. Evaluation of a subcutaneous glucose sensor out to 3 months in a dog model. *Diabetes Care*, 17(8):882-887.

Gilligan, B. C.; Shults, M.; Rhodes, R. K.; Jacobs, P. G.; Brauker, J. H.; Pintar, T. J.; Updike, S. J. Feasibility of continuo long-term glucose monitoring from a subcutaneous glucose sensor in humans. Diabetes Technol Ther 2004, 6, 378-386.

Heise, et al. 2003. Hypoglycemia warning signal and glucose sensors: Requirements and concepts. *Diabetes Technology & Therapeutics*, 5:563-571.

Heller, A. Implanted electrochemical glucose sensors for the management of diabetes. Annu Rev Biomed Eng 1999, 1, 153-175.

Kraver, K.; Gutha, M. R.; Strong, T.; Bird, P.; Cha, G.; Hoeld, W.; Brown, R. A mixed-signal sensor interface microinstrument. Sensors and Actuators A: Physical 2001, 91, 266-277.

Sansen, et al. 1990. A smart sensor for the voltammetric measurement of oxygen or glucose concentrations. *Sensors and Actuators*, B 1:298-302.

Sriyudthsak, M.; Cholapranee, T.; Sawadsaringkarn, M.; Yupongchaey, N.; Jaiwang, P. Enzyme-epoxy membrane based glucose analyzing system and medical applications. Biosens Bioelectron 1996, 11, 735-742.

Tierney, M. J.; Garg, S.; Ackerman, N. R.; Fermi, S. J.; Kennedy, J.; Lopatin, M.; Potts, R. O.; Tamada, J. A. Effect of acetaminophen on the accuracy of glucose measurements obtained with the GlucoWatch biographer. Diabetes Technol Ther 2000, 2, 199-207.

Updike et al. 1994. Improved long-term performance in vitro and in vivo. *ASAIO Journal*, 40(2):157-163.

Updike et al. 1997. Principles of long-term fully implanted sensors with emphasis on radiotelemetric monitoring of blood glucose from inside a subcutaneous foreign body capsule (FBC). In Fraser, D. M. (Ed.). Biosensors in the Body: Continuous in vivo Monitoring. Chap. 4, pp. 117-137, Hoboken, NJ: John Wiley.

Updike, et al. 2000. A subcutaneous glucose sensor with improved longevity, dynamic range, and stability of calibration. *Diabetes Care*, 23(2):208-214.

Valdes, et al. 2000. In vitro and in vivo degradation of glucose oxidase enzyme used for an implantable glucose biosensor. *Diabetes Technol. Ther.*, 2:367-376.

Wagner, et al. 1998. Continuous amperometric monitoring of glucose in a brittle diabetic chimpanzee with a miniature subcutaneous electrode. *Proc. Natl. Acad. Sci. A*, 95:6379-6382.

Ward, et al. 1999. Assessment of chronically implanted subcutaneous glucose sensors in dogs: The effect of surrounding fluid masses. *ASAIO Journal*, 45:555-561.

Ward, W. K.; Wood, M. D.; Troupe, J. E. Understanding Spontaneous Output Fluctuations of an Amperometric Glucose Sensor: Effect of Inhalation Anesthesia and Use of a Nonenzyme Containing Electrode. ASAIO Journal 2000, 540-546.

Ward, et al. 2000. Rise in background current over time in a subcutaneous glucose sensor in the rabbit: Relevance to calibration and accuracy. *Biosensors & Bioelectronics*, 15:53-61.

Ward et al. 2002. A new amperometric glucose microsensor: In vitro and short-term in vivo evaluation. *Biosensors & Bioelectronics*, 17:181-189.

Wilkins, et al. 1995. Integrated implantable device for long-term glucose monitoring. *Biosens. Bioelectron.*, 10:485-494.

Wientjes, K. J. C. Development of a glucose sensor for diabetic patients. 2000.

Wilkins, E.; Atanasov, P. Glucose monitoring: state of the art and future possibilities. Med Eng Phys 1995, 18, 273-288.

Wilson, et al. 1992. Progress toward the development of an implantable sensor for glucose. *Clin. Chem.*, 38(9):1613-1617.

Wood, W., et al., Hermetic Sealing with Epoxy. Mechanical Engineering Mar. 1990, 1-3.

U.S. Appl. No. 09/447,227, filed Nov. 22, 1999, (See Image File Wrapper).

U.S. Appl. No. 10/838,658, filed May 3, 2004, (See Image File Wrapper).

U.S. Appl. No. 10/838,909, filed May 3, 2004, (See Image File Wrapper).

U.S. Appl. No. 10/838,912, filed May 3, 2004, (See Image File Wrapper).

U.S. Appl. No. 10/885,476, filed Jul. 6, 2004, (See Image File Wrapper).

U.S. Appl. No. 10/896,312, filed Jul. 21, 2004, (See Image File Wrapper).

Bard et al. 1980. Electrochemical Methods. John Wiley & Sons, pp. 173-175.

Bott, A. W. 1997. A Comparison of Cyclic Voltammetry and Cyclic Staircase Voltammetry Current Separations 16:1, 23-26.

Brooks, et al. "Development of an on-line glucose sensor for fermentation monitoring," Biosensors, 3:45-56 (1987/88).

Frohnauer, et al. 2001. Graphical human insulin time-activity profiles using standardized definitions. Diabetes Technology & Therapeutics 3(3):419-429.

Heller, "Electrical wiring of redox enzymes," Acc. Chem. Res., 23:128-134 (1990).

Kerner, et al. "The function of a hydrogen peroxide-detecting electroenzymatic glucose electrode is markedly impaired in human sub-cutaneous tissue and plasma," Biosensors & Bioelectronics, 8:473-482 (1993).

Koschinsky, et al. 1998. New approach to technical and clinical evaluation of devices for self-monitoring of blood glucose. Diabetes Care 11(8): 619-619.

Mastrototaro, et al. "An electroenzymatic glucose sensor fabricated on a flexible substrate," Sensors and Actuators B, 5:139-44 (1991).

Moatti-Sirat, D, et al. 1992. Evaluating in vitro and in vivo the interference of ascorbate and acetaminophen on glucose detection by a needle-type glucose sensor. Biosensors and Bioelectronics 7:345-352.

Pickup, et al. "Implantable glucose sensors: choosing the appropriate sensor strategy," *Biosensors*, 3:335-346 (1987/88).

Pickup, et al. "In vivo molecular sensing in diabetes mellitus: an implantable glucose sensor with direct electron transfer," *Diabetologia*, 32:213-217 (1989).

Rebrin, et al. "Automated feedback control of subcutaneous glucose concentration in diabetic dogs," Diabetologia, 32:573-76 (1989).

Shaw, et al. "In vitro testing of a simply constructed, highly stable glucose sensor suitable for implantation in diabetic patients," Biosensors & Bioelectronics, 6:401-406 (1991).

Turner and Pickup, "Diabetes mellitus: biosensors for research and management," Biosensors, 1:85-115 (1985).

Office Action dated Sep. 5, 2006 in U.S. Appl. No. 09/916,711.
Office Action dated Feb. 14, 2006 in U.S. Appl. No. 09/916,711.
Office Action dated Jul. 1, 2005 in U.S. Appl. No. 09/916,711.
Office Action dated Jul. 23, 2004 in U.S. Appl. No. 09/916,711.
Office Action dated Dec. 23, 2004 in U.S. Appl. No. 09/916,711.
Office Action dated Feb. 11, 2004 in U.S. Appl. No. 09/916,711.
Office Action dated Sep. 24, 2003 in U.S. Appl. No. 09/916,711.
Office Action dated Dec. 7, 1998 in U.S. Appl. No. 08/811,473.
Office Action dated Jul. 17, 2007 in U.S. Appl. No. 09/447,227.
Office Action dated Mar. 9, 2007 in U.S. Appl. No. 09/447,227.
Office Action dated Aug. 1, 2006 in U.S. Appl. No. 09/447,227.
Office Action dated Apr. 4, 2006 in U.S. Appl. No. 09/447,227.
Office Action dated Sep. 22, 2005 in U.S. Appl. No. 09/447,227.
Office Action dated Nov. 28, 2003 in U.S. Appl. No. 09/447,227.
Office Action dated Jul. 9, 2003 in U.S. Appl. No. 09/447,227.
Office Action dated Jan. 16, 2003 in U.S. Appl. No. 09/447,227.
Office Action dated Jul. 15, 2002 in U.S. Appl. No. 09/447,227.
Office Action dated Jan. 17, 2002 in U.S. Appl. No. 09/447,227.
Office Action dated Aug. 15, 2001 in U.S. Appl. No. 09/447,227.
Office Action dated Feb. 24, 2006 in U.S. Appl. No. 10/646,333.
Office Action dated Jun. 6, 2003 in U.S. Appl. No. 10/646,333.
Office Action dated Sep. 22, 2004 in U.S. Appl. No. 09/646,333.
Office Action dated May 22, 2006 in U.S. Appl. No. 10/896,772.
Office Action dated Dec. 14, 2005 in U.S. Appl. No. 10/896,772.
Office Action dated Jul. 19, 2005 in U.S. Appl. No. 10/896,772.
Office Action dated Jan. 11, 2005 in U.S. Appl. No. 10/896,772.
Office Action dated May 11, 2006 in U.S. Appl. No. 10/897,377.
Office Action dated Oct. 18, 2005 in U.S. Appl. No. 10/897,377.
Office Action dated Feb. 9, 2006 in U.S. Appl. No. 10/897,312.
Office Action dated Jan. 27, 2006 in U.S. Appl. No. 11/007,635.
Office Action mailed May 18, 2007 in U.S. Appl. No. 11/543,707.
Office Action mailed May 23, 2007 in U.S. Appl. No. 11/543,539.
Office Action mailed May 18, 2007 in U.S. Appl. No. 11/543,683.
Office Action mailed Jun. 5, 2007 in U.S. Appl. No. 11/543,734.
Office Action dated Sep. 21, 2007 in U.S. Appl. No. 10/838,912.
Office Action dated May 17, 2007 in U.S. Appl. No. 11/077,759.
Office Action dated Jul. 26, 2007 in U.S. Appl. No. 11/077,715.
Office Action dated Apr. 10, 2007 in U.S. Appl. No. 11/077,715.
Office Action dated Oct. 31, 2006 in U.S. Appl. No. 11/077,715.

Office Action dated Jul. 27, 2007 in U.S. Appl. No. 11/077,714.
Office Action dated Apr. 10, 2007 in U.S. Appl. No. 11/077,714.
Office Action dated Oct. 11, 2006 in U.S. Appl. No. 11/077,714.
Office Action dated Jan. 30, 2007 in U.S. Appl. No. 11/077,763.
Office Action dated Oct. 9, 2007 in U.S. Appl. No. 11/077,883.
Office Action dated Sep. 18, 2007 in U.S. Appl. No. 11/078,230.
Cass, et al. "Ferrocene-mediated enzyme electrodes for amperometric determination of glucose," Anal. Chem., 36:667-71 (1984).
Godsland, et al. 2001. Maximizing the Success Rate of Minimal Model Insulin Sensitivity Measurement in Humans: The Importance of Basal Glucose Levels. The Biochemical Society and the Medical Research Society, 1-9.
Rhodes, et al. 1994. Prediction of pocket-portable and implantable glucose enzyme electrode performance from combined species permeability and digital simulation analysis. Analytical Chemistry 66(9):1520-1529.
Wientjes, K. J. C. 2000. Development of a glucose sensor for diabetic patients (Ph.D. Thesis).
Wilkins, et al. 1995. Integrated implantable device for long-term glucose monitoring. Biosens. Bioelectron 10:485-494.
Office Action dated Jan. 23, 2008 in U.S. Appl. No. 09/447,227.
Office Action dated Dec. 26, 2007 in U.S. Appl. No. 11/021,046.
Office Action dated Sep. 30, 2002 in U.S. Appl. No. 09/636,369.
Office Action dated Nov. 28, 2007 in U.S. Appl. No. 10/991,966.
Office Action dated Nov. 27, 2006 in U.S. Appl. No. 10/789,359.
Office Action dated Dec. 12, 007 in U.S. Appl. No. 11/543,707.
Office Action mailed Dec. 12, 2007 in U.S. Appl. No. 11/543,539.
Office Action mailed Dec. 12, 2007 in U.S. Appl. No. 11/543,683.
Office Action mailed Dec. 17, 2007 in U.S. Appl. No. 11/543,734.
Office Action dated Jan. 15, 2008 in U.S. Appl. No. 11/034,344.
Office Action dated Jan. 28, 2008 in U.S. Appl. No. 11/077,715.
Office Action dated Jan. 10, 2008 in U.S. Appl. No. 11/077,714.
Office Action dated Jan. 3, 2008 in U.S. Appl. No. 11/,157,746.
Office Action dated Sep. 25, 2007 in U.S. Appl. No. 11/334,876.
Office Action dated Oct. 4, 2006 in U.S. Appl. No. 11/334,876.

* cited by examiner

COMPOSITE MATERIAL FOR IMPLANTABLE DEVICE

RELATED APPLICATIONS

This application claims the benefit of U.S. Provisional Application No. 60/535,885, filed Jan. 12, 2004, and U.S. Provisional Application No. 60/535,914 filed Jan. 12, 2004, both of which are incorporated by reference herein in their entirety, and both of which are hereby made a part of this specification.

FIELD OF THE INVENTION

The present invention relates generally to a composite material for an implantable device and systems and methods for its manufacturing.

BACKGROUND OF THE INVENTION

A variety of implantable medical devices are known in the art for purposes such as sensors for diagnostic testing, blood pumps, pacemakers, and the like. Many of these devices transmit and receive information via Radio Frequency (RF) through or from a patient's body to a location remote therefrom. Some of these devices are formed from hermetic materials (e.g., titanium) in order to protect the sensitive RF components from the effects that can occur to an implanted medical device in vivo, for example, due to moisture penetration. Unfortunately, this design suffers from complexity of design and manufacture and/or higher density and mass than otherwise necessary.

SUMMARY OF THE INVENTION

In a first embodiment, a device suitable for implantation in a body of a host is provided, the device comprising a composite material comprising a matrix material and a plurality of hollow gas-filled beads.

In an aspect of the first embodiment, the beads are glass beads.

In an aspect of the first embodiment, the matrix material comprises a polymeric material, for example, an epoxy.

In an aspect of the first embodiment, the device comprises a body that is at least partially formed by mixing the matrix material and the hollow gas-filled beads to form a mixture, and curing the mixture.

In an aspect of the first embodiment, a diameter of at least a portion of the beads is from about 0.001 mm to about 3 mm.

In an aspect of the first embodiment, a diameter of at least a portion of the beads is about 1 mm or less.

In an aspect of the first embodiment, the device further comprises an antenna for radiating or receiving an RF transmission. The composite material can be proximal to the antenna or adjacent to the antenna.

In an aspect of the first embodiment, a dielectric constant of the composite material is less than a dielectric constant of the matrix material.

In a second embodiment, a method for forming a composite material suitable for implantation in a host is provided, the method comprising providing a matrix material having a first dielectric constant; providing a plurality of hollow gas-filled beads having a second dielectric constant, wherein the second dielectric constant is lower than the first dielectric constant; mixing the hollow gas-filled beads and the matrix material to obtain a mixture; and curing the mixture, whereby a composite material with a third dielectric constant is formed, wherein the third dielectric constant is lower than the first dielectric constant and higher than the second dielectric constant.

In an aspect of the second embodiment, the gas-filled beads are air-filled beads.

In an aspect of the second embodiment, the implantable device comprises electronics and an antenna for radiating or receiving a RF transmission, and wherein the step of curing comprises curing the mixture proximal to the antenna. The step of curing can comprise at least partially encapsulating the electronics and the antenna with the composite material.

In an aspect of the second embodiment, the implantable device comprises a glucose sensor.

In a third embodiment, a device suitable for implantation in a host is provided, the device comprising a body and electronics, wherein the overall density of the device is about 1 $g/cm^3$.

In an aspect of the third embodiment, the body is formed from a composite material comprising a matrix material and a plurality of hollow gas-filled beads. The composite material can have an overall density of less than about 1 $g/cm^3$.

In an aspect of the third embodiment, the device is configured to measure glucose.

In an aspect of the third embodiment, the device is a wholly implantable glucose sensor configured for implantation in a subcutaneous tissue of a host.

DETAILED DESCRIPTION OF THE PREFERRED EMBODIMENT

Figure 1:
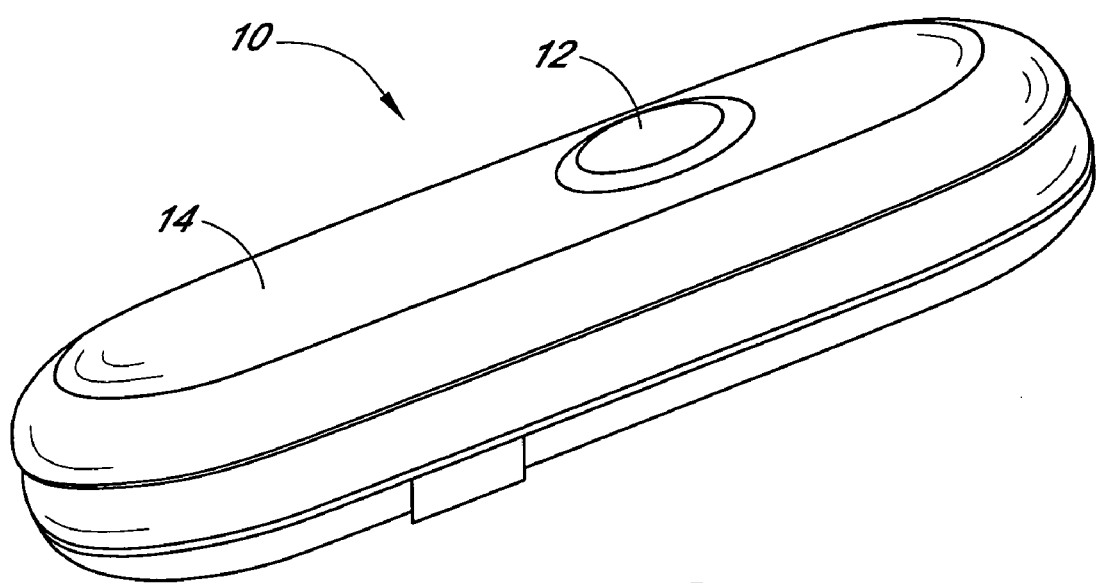
FIG. 1 is a perspective view of a system that utilizes a composite material of the preferred embodiments.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

DEFINITIONS

In order to facilitate an understanding of the preferred embodiments, a number of terms are defined below.

The term "host," as used herein, is a broad term and is used in its ordinary sense, including, but not limited to, mammals such as humans.

The term "matrix material," as used herein, is a broad term and is used in its ordinary sense, including, but not limited to, the continuous phase in a composite material in which a second phase is dispersed. In the preferred embodiments, the matrix material is a material that can be provided in liquid or powder form and cured to form a relatively solid body. Matrix materials suitable for the preferred embodiments include: insulating materials, water-vapor permeable materials, and polymeric materials, such as epoxies, urethanes, silicones, resins, Parylene, and the like.

The term "beads" as used herein, is a broad term and is used in its ordinary sense, including, without limitation, bubbles or other hollow or enclosed spaces filled with a gas, a vacuum, or low-density material (wherein the density is compared to that of the matrix material).

The term "RF transceiver," as used herein, is a broad term and is used in its ordinary sense, including, but not limited to, a radio frequency transmitter and/or receiver for transmitting and/or receiving signals.

The term "antenna," as used herein, is a broad term and is used in its ordinary sense, including, but not limited to, a metallic or conductive device (such as a rod or wire) for radiating or receiving radio waves.

The terms "raw data stream" and "data stream," as used herein, are broad terms and are used in their ordinary sense, including, but not limited to, an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, 3, 4, or 5 minutes or longer.

The term "electronic circuitry," as used herein, is a broad term and is used in its ordinary sense, including, but not limited to, the components (for example, hardware and/or software) of a device configured to process data. In the case of a glucose sensor, the data includes biological information obtained by a sensor regarding the concentration of the analyte in a biological fluid.

The terms "operably connected" and "operably linked," as used herein, are broad terms and are used in their ordinary sense, including, but not limited to, one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

Overview

Implantable devices are disclosed in the preferred embodiments, which utilize a composite material that allows for optimization of the density and/or overall weight of the implantable device. Polymeric materials, for example epoxy, can be used to encapsulate implantable devices; however these polymeric materials can have a sub-optimal weight and/or density for implantation. Most implantable devices are denser than the body and therefore tend to migrate when implanted. Migration can increase the local inflammatory response of the body to the device, which can result in altered function of the implantable device, such as is described in co-pending U.S. patent application Ser. No. 10/646,333, which is incorporated herein by reference in its entirety. Therefore, it can be advantageous to decrease the density (and/or weight) of the implantable device, such as described in more detail below.

Additionally, the implantable device of the preferred embodiments, including the composite material described herein, can optimize RF performance when the implantable device utilizes RF transmissions; for example, implantable devices that are encapsulated in a polymeric material (e.g., epoxy), particularly where the polymeric material comes into direct or close contact with the antenna. These devices typically use electrically small antennas, which tend to have a high Q (Quality factor) making the antenna resonant frequency shift strongly depending on the environment (e.g., dielectric constant of the encapsulating material can shift over time as moisture penetrates through the encapsulating material and proximal to the antenna). Unfortunately, this shift in frequency response can cause the efficiency of the antenna to change when it becomes encapsulated within an implantable device and implanted inside the body (e.g., due to moisture penetration through a moisture-permeable encapsulating material, such as epoxy). Therefore, it can be advantageous to improve the efficiency of the antenna by maintaining a substantially constant dielectric property of the device surrounding the antenna over time even when implanted in a host body.

Accordingly, implantable devices are provided wherein the implantable devices include a composite material formed from a matrix material and a plurality of beads incorporated therein. In some embodiments, the composite material encapsulates or substantially encapsulates the electronic circuitry (components) of an implantable device to form the body of device (or a portion of the body of the device). Preferably, the beads can be mixed with the matrix material (e.g., epoxy) prior to curing, and can be very small (e.g., smaller than $\frac{1}{1000}^{th}$ of an inch). These small beads are hollow and can be filled with any number of gases or a vacuum.

In preferred embodiments, the matrix material can be any material that can be provided in liquid or powder form and cured to form a relatively solid body. Matrix materials particularly suitable for use in the preferred embodiments include insulating materials, water-vapor permeable materials, and polymeric materials, such as epoxies, urethanes, silicones, resins, Parylene, and the like. In some embodiments, epoxy materials are generally preferred as the matrix material. However, any suitable material can be employed, for example, other polymeric materials, metals, ceramics, glasses, and the like, as will be appreciated by one skilled in the art.

While hollow, or air filled, glass beads are generally preferred, any suitable material of reduced dielectric content or reduced density, when compared to that of the matrix material, can be employed. For example, hollow epoxy beads, or hollow beads prepared from another material, such as polymeric, ceramic, or metallic materials, can also be employed. In addition to hollow beads, beads comprising encapsulated open celled foam, or encapsulated or unencapsulated closed cell foam can also be employed. For example, expandable polystyrene beads can be employed. While beads are generally preferred, any suitable shape can be employed, for example, cubes, rods, irregular shapes, and the like.

The beads or other fill material can be of any suitable size. Preferably, the beads range in size from a few microns or smaller to a few millimeters or larger in their greatest dimension. Generally, filler having particle sizes of from about 0.001 mm, 0.005, 0.01, 0.05, 0.1, or 0.5 mm to about 1, 2, or 3 mm are generally preferred. A variety of sizes and shapes of filler particles can be mixed together to improve the number of particles that can be packed into a certain volume.

In some alternative embodiments, the composite material can employ an epoxy or other polymeric foam, wherein the voids are filled with a gas or a vacuum. The composite material comprises gas-filled voids that aid in reducing the weight and/or density of the matrix material and/or additionally reduce the dielectric constant surrounding the antenna.

In practice, the beads are added to the matrix material, and the material is cured or hardened to form a body, such as the entire implantable device body or a portion thereof. In some embodiments, the beads can be added to a matrix material in its liquid phase (e.g., liquid epoxy) before or after a hardener is added. When a light or UV cure is chosen to cure the matrix material, the beads can be added at any time prior to the hardening of the matrix material. Once a desired amount of beads are added to the matrix material, they are mixed, and the material is cured to form the body (or portion of the body) of the implantable device. The resulting structure of the composite material (namely, matrix material and beads) can be optimized for density, RF performance, and other characteristics such as described in more detail below.

Implantable devices can be tailored to a wide variety of desirable weights and/or densities using the composite material of the preferred embodiments. This composite material (e.g., with a density less than 1 g/cm$^3$) can provide an advantage of offsetting the electronics (e.g., with density more than 1 g/cm$^3$) to achieve an implantable device with an overall density of about 1 g/cm$^3$. An implantable device with a density of about 1 g/cm$^3$ effectively "floats" within the tissue of the body. Thus, as the body experiences sudden accelerations and decelerations (e.g., jumping, car rides, running, and the like) the device does not experience a displacing force, which would otherwise cause motion artifact, which is known to increase local inflammatory response and decrease device function in many uses and applications. Furthermore, it is contemplated that the device can be implanted without any anchoring device, or that the existing anchoring devices provide sufficient function to counteract motion artifact.

Additionally, the tuning of an RF antenna in an implantable device can be more robust due to a more consistent dielectric property surrounding an antenna within the implantable device. Namely, the composite material (e.g., matrix material and gas-filled beads) effectively maintains a reduced dielectric constant as compared with matrix material only because the beads (being hollow) add air to the composite structure and therefore lower the dielectric constant of the surrounding body (e.g., closer to the environment in which the antenna was tuned) such that a substantially constant dielectric property is maintained over time in vivo.

While the composite materials of the preferred embodiments are particularly well suited for use in conjunction with implantable glucose sensors, they can also be employed in any other implantable device wherein neutral buoyancy, low dielectric constant, or some other characteristic feature is desirable, for example, pacemakers, sensors, prostheses, and the like.

Exemplary Continuous Glucose Sensor Configuration

FIG. 1 is a perspective view of a system that utilizes a composite material of the preferred embodiments. It includes a continuous glucose sensor 10 implanted within a human and can be configured for transmitting data via RF in some embodiments. The system of the preferred embodiments provides reduced density for improved interaction within the physiological environment and reliable RF transmissions through the physiological environment, thereby increasing overall patient confidence, safety, and convenience.

The continuous glucose sensor 10 measures a concentration of glucose or a substance indicative of a concentration or a presence of glucose. However, the concepts described with reference to the sensor 10 can be implemented with any sensor capable of determining the level of any analyte in the body, for example, oxygen, lactase, insulin, hormones, cholesterol, medicaments, viruses, or the like. Additionally, although much of the description of the glucose sensor is focused on electrochemical detection methods, the systems and methods can be applied to glucose sensors that utilize other measurement techniques, including enzymatic, chemical, physical, spectrophotometric, polarimetric, calorimetric, radiometric, or the like.

Reference is now made to FIG. 1, which is a perspective view of the implantable glucose sensor 10 of the preferred embodiments. Co-pending U.S. patent application Ser. No. 10/838,912, filed May 3, 2004 and entitled, "IMPLANTABLE ANALYTE SENSOR" and U.S. Patent Publication No. 2003-0032874 A1 disclose systems and methods that can be used with this exemplary glucose sensor embodiment. In this embodiment, a sensing region 12 is shown on the body 14 of the glucose sensor 10. In one preferred embodiment, the sensing region 12 comprises an electrode system including a platinum working electrode, a platinum counter electrode, and a silver/silver chloride reference electrode. However, a variety of electrode materials and configurations can be used with the implantable glucose sensors of the preferred embodiments. The top ends of the electrodes are in contact with an electrolyte phase (not shown), which is a free-flowing fluid phase disposed between a sensing membrane and the electrodes. In one embodiment, the counter electrode is provided to balance the current generated by the species being measured at the working electrode. In some embodiments, the sensing membrane includes an enzyme, for example, glucose oxidase, and covers the electrolyte phase. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

Glucose+$O_2$→Gluconate+$H_2O_2$

The change in $H_2O_2$ can be monitored to determine glucose concentration, because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons (2$H^+$), two electrons (2$e^-$), and one oxygen molecule ($O_2$).

A potentiostat is employed to monitor the electrochemical reaction at the electroactive surface(s). The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose value.

Figure 2:
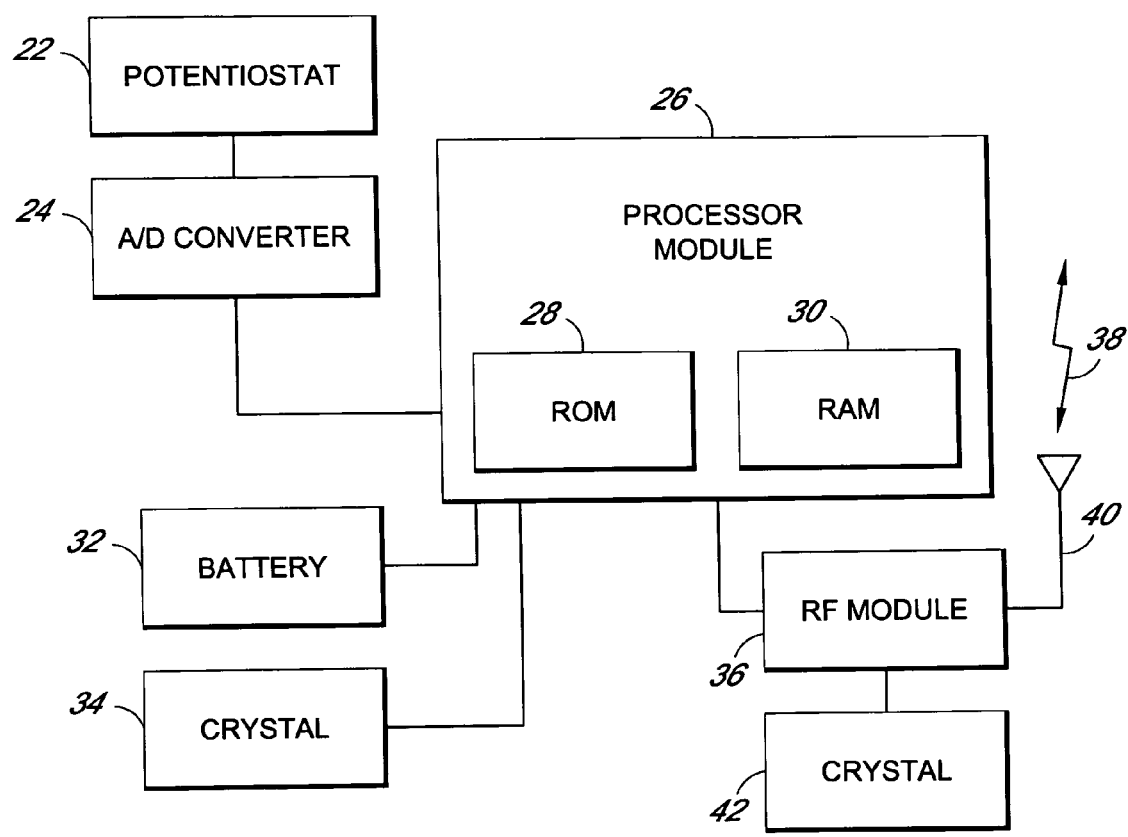
FIG. 2 is a block diagram that illustrates the electronics associated with the implantable glucose sensor in one embodiment.

FIG. 2 is a block diagram that illustrates the electronics 20 associated with the implantable glucose sensor 10 in one embodiment. In this embodiment, a potentiostat 22 is shown, which is operably connected to an electrode system (such as described above) to obtain a current value, and includes a resistor (not shown) that translates the current into voltage. An A/D converter 24 digitizes the analog signal into "counts" for processing. Accordingly, the resulting raw data stream in counts is directly related to the current measured by the potentiostat 22.

A processor module 26 includes the central control unit that houses ROM 28 and RAM 30 and controls the processing of the sensor electronics 20. In some embodiments, the processor module includes a microprocessor, however a computer system other than a microprocessor can be used to process data as described herein, for example an application-specific integrated circuit (ASIC) can be used for some or all of the sensor's central processing, as is appreciated by one skilled in the art. The ROM 28 provides semi-permanent storage of data, for example, storing data such as sensor identifier (ID) and programming to process data streams (for example, programming for data smoothing and/or replacement of signal artifacts such as described in copending U.S. patent application Ser. No. 10/648,849, filed Aug. 22, 2003, and entitled, "SYSTEMS AND METHODS FOR REPLACING SIGNAL ARTIFACTS IN A GLUCOSE SENSOR DATA STREAM," which is incorporated herein by reference in its entirety). The RAM 30 can be used for the system's cache memory, for example, for temporarily storing recent sensor data. In some alternative embodiments, memory storage components comparable to ROM 28 and RAM 30 can be used instead of or in addition to the preferred hardware, such as dynamic-RAM, static-RAM, non-static RAM, EEPROM, rewritable ROMs, flash memory, or the like.

A battery 32 is operably connected to the sensor electronics 20 and provides the necessary power for the sensor 10. In one embodiment, the battery is a lithium manganese dioxide battery; however any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable. In some embodiments, a plurality of batteries can be used to power the system. In yet other embodiments, the sensor can be transcutaneously powered via an inductive coupling, for example. In some embodiments, a quartz crystal 34 is operably connected to the processor 26 and maintains system time for the computer system as a whole.

An RF module 36 is operably connected to the processor 26 and transmits the sensor data from the sensor 10 to a receiver (not shown) within a wireless transmission 38 via antenna 40. In some embodiments, a second quartz crystal 42 provides the system time for synchronizing the data transmissions from the RF transceiver. In some alternative embodiments, however, other mechanisms, such as optical, infrared radiation (IR), ultrasonic, or the like can be used to transmit and/or receive data.

In the configuration of the RF telemetry module of the preferred embodiments, the hardware and software are designed for low power requirements to increase the longevity of the device (for example, to enable a life of up to 3 to 24 months, or more) with maximum RF transmittance from the in vivo environment to the ex vivo environment (for example, about one to ten meters). Preferably, a high frequency carrier signal in the range of 402 to 405 MHz is employed in order to maintain lower power requirements. Additionally, the carrier frequency is adapted for physiological attenuation levels, which is accomplished by tuning the RF module in a simulated in vivo environment to ensure RF functionality after implantation. Accordingly, it is believed that the preferred glucose sensors can sustain sensor function for 3 months, 6 months, 12 months, 24 months, or more.

Additionally, the exemplary glucose sensor comprises the composite material of the preferred embodiments. In one embodiment, the body of the sensor is preferably formed from a composite of epoxy mixed with glass beads and molded around the sensor electronics; however, in alternative embodiments, the body can be formed from a variety of composite materials; for example, other matrix materials can also be used, such as silicone, urethane, or other polymeric materials, as well as other types of beads. Co-pending U.S. patent application Ser. No. 10/838,909, filed May 3, 2004 and entitled, "IMPLANTABLE MEDICAL DEVICE," which is incorporated herein by reference in its entirety, describes systems and methods for encapsulation of sensor electronics in a water vapor permeable material, such as epoxy, which systems and methods can be implemented with the preferred embodiments for encapsulation of an implantable device in the composite material of the preferred embodiments.

While not wishing to be bound by theory, it is believed that implantable devices that are partially or wholly formed from the composite material of the preferred embodiments minimize the local inflammatory response of the body to the device, which can result in improved function of the implantable device. Additionally, it is believed that implantable devices that are partially or wholly formed from the composite material of the preferred embodiments improve the tuning of the antenna by lowering the dielectric constant surrounding the antenna, thereby minimizing the susceptibility of the antenna to change as it becomes encapsulated within an implantable device.

While the systems and methods of the preferred embodiments are particularly well suited for use in conjunction with implantable glucose sensors, they can also be employed in any other implantable devices wherein neutral buoyancy, low dielectric constant, or some other characteristic feature is desirable, for example, pacemakers, sensors, prostheses, and the like.

EXAMPLE

An experiment was performed wherein four different amounts of glass beads were each added to three grams of epoxy, after which the material was cured and their densities measured. The results in Table 1 were then graphed to show the weight percent loading to density relationship of the glass beads in epoxy.

TABLE 1

| Sample | epoxy weight (g) | glass spheres (g) | diameter (mm) | volume (ml$^3$) | mass (g) | density (g/ml$^3$) | wt. % loading |
|---|---|---|---|---|---|---|---|
| 1 | 3.00 | 0.150 | 35.74 | 3.43418 | 2.5896 | 0.7541 | 4.8 |
| 2 | 3.00 | 0.300 | 35.76 | 4.58403 | 2.9779 | 0.6496 | 9.1 |
| 3 | 3.00 | 0.447 | 35.78 | 5.13549 | 2.8506 | 0.5551 | 13.0 |
| 4 | 3.00 | 0.599 | 35.74 | 5.01499 | 2.4824 | 0.4950 | 16.6 |

Figure 3:
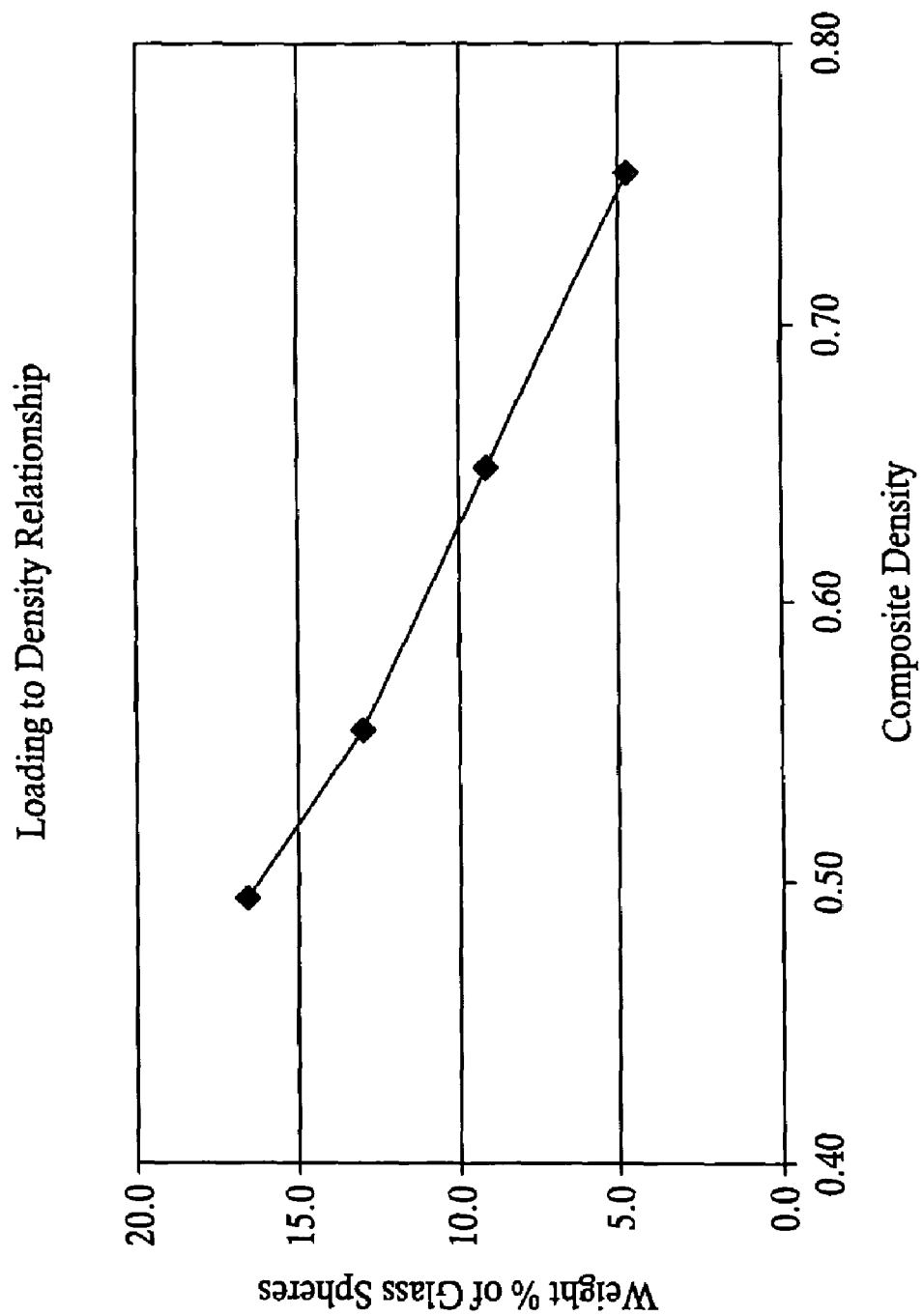
FIG. 3 is a graph that illustrates the relationship between loading and density determined from an experiment comparing composite materials of the preferred embodiments.

FIG. 3 is a graph that illustrates the relationship between loading and density determined from the above-described experiment. The x-axis represents the density of the composite material in g/ml$^3$. The y-axis represents the weight % of glass beads (spheres). The graph shows that the addition of 17 weight percent glass beads to the epoxy reduces the density of the epoxy to about 0.5 g/ml$^3$. The density of the epoxy material without the addition of the glass beads is about 1.1 g/ml$^3$. This represents a 55% reduction in density of the composite material as compared to epoxy alone. A much lower or higher weight percent of glass beads can be added to the epoxy than is shown above. While not wishing to be bound by theory, it is believed that the density of the composite mixture can be reduced to about 10% of the density of normal epoxy, for example.

Methods and devices that are suitable for use in conjunction with aspects of the preferred embodiments are disclosed in co-pending U.S. patent application Ser. No. 10/885,476, filed Jul. 6, 2004, and entitled "SYSTEMS AND METHODS FOR MANUFACTURE OF AN ANALYTE SENSOR INCLUDING A MEMBRANE SYSTEM"; U.S. patent application Ser. No. 10/842,716, filed May 10, 2004, and entitled, "MEMBRANE SYSTEMS INCORPORATING BIOACTIVE AGENTS"; co-pending U.S. patent application Ser. No. 10/838,912, filed May 3, 2004, and entitled, "IMPLANTABLE ANALYTE SENSOR"; U.S. patent application Ser. No. 10/789,359, filed Feb. 26, 2004, and entitled, "INTEGRATED DELIVERY DEVICE FOR A CONTINUOUS GLUCOSE SENSOR"; U.S. application Ser. No. 10/685,636, filed Oct. 28, 2003, and entitled, "SILICONE COMPOSITION FOR MEMBRANE SYSTEM"; U.S. application Ser. No. 10/648,849, filed Aug. 22, 2003, and entitled, "SYSTEMS AND METHODS FOR REPLACING SIGNAL ARTIFACTS IN A GLUCOSE SENSOR DATA STREAM"; U.S. application Ser. No. 10/646,333, filed Aug. 22, 2003 entitled, "OPTIMIZED SENSOR GEOMETRY FOR AN IMPLANTABLE GLUCOSE SENSOR"; U.S. application Ser. No. 10/647,065, filed Aug. 22, 2003, entitled, "POROUS MEMBRANES FOR USE WITH IMPLANTABLE DEVICES"; U.S. application Ser. No. 10/633,367, filed Aug. 1, 2003, entitled, "SYSTEM AND METHODS FOR PROCESSING ANALYTE SENSOR DATA"; U.S. Pat. No. 6,702,857 entitled "MEMBRANE FOR USE WITH IMPLANTABLE DEVICES"; U.S. application Ser. No. 09/447,227, filed Nov. 22, 1999, and entitled "DEVICE AND METHOD FOR DETERMINING ANALYTE LEVELS"; and U.S. Publ. No. 2004-0011671 A1 entitled "DEVICE AND METHOD FOR DETERMINING ANALYTE LEVELS," as well as published applications and issued patents including U.S. Publ. No. 2003/0217966 A1 entitled "TECHNIQUES TO IMPROVE POLYURETHANE MEMBRANES FOR IMPLANTABLE GLUCOSE SENSORS"; U.S. Publ. No. 2003/0032874 A1 entitled "SENSOR HEAD FOR USE WITH IMPLANTABLE DEVICE"; U.S. Pat. No. 6,741,877 entitled "DEVICE AND METHOD FOR DETERMINING ANALYTE LEVELS"; U.S. Pat. No. 6,558,321 entitled "SYSTEMS AND METHODS FOR REMOTE MONITORING AND MODULATION OF MEDICAL DEVICES"; U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE"; U.S. Appl. No. 60/489,615 filed Jul. 23, 2003 and entitled "ROLLED ELECTRODE ARRAY AND ITS METHOD FOR MANUFACTURE"; U.S. Appl. No. 60/490,010 filed Jul. 25, 2003 and entitled "INCREASING BIAS FOR OXYGEN PRODUCTION IN AN ELECTRODE ASSEMBLY"; U.S. Appl. No. 60/490,009 filed Jul. 25, 2003 and entitled "OXYGEN ENHANCING ENZYME MEMBRANE FOR ELECTROCHEMICAL SENSORS"; U.S. application Ser. No. 10/896,312 filed Jul. 21, 2004 and entitled "OXYGEN-GENERATING ELECTRODE FOR USE IN ELECTROCHEMICAL SENSORS"; U.S. application Ser. No. 10/896,637 filed Jul. 21, 2004 and entitled "ROLLED ELECTRODE ARRAY AND ITS METHOD FOR MANUFACTURE"; U.S. application Ser. No. 10/896,772 filed Jul. 21, 2004 and entitled "INCREASING BIAS FOR OXYGEN PRODUCTION IN AN ELECTRODE ASSEMBLY"; U.S. application Ser. No. 10/896,639 filed Jul. 21, 2004 and entitled "OXYGEN ENHANCING ENZYME MEMBRANE FOR ELECTROCHEMICAL SENSORS"; U.S. application Ser. No. 10/897,377 filed Jul. 21, 2004 and entitled "ELECTROCHEMICAL SENSORS INCLUDING ELECTRODE SYSTEMS WITH INCREASED OXYGEN GENERATION". The foregoing patent applications and patents are hereby incorporated herein by reference in their entireties.

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A device suitable for implantation in a body of a host, the device comprising a composite material comprising a matrix material and a plurality of hollow gas-filled beads, wherein a dielectric constant of the composite material is less than a dielectric constant of the matrix material, the device further comprising an antenna that is configured for wireless communication and that is substantially encapsulated by the composite material, and wherein the composite material is configured to enhance tuning of the antenna.

2. The device of claim 1, wherein the beads are glass beads.

3. The device of claim 1, wherein the matrix material comprises a polymeric material.

4. The device of claim 3, wherein the polymeric material comprises an epoxy.

5. The device of claim 1, wherein the device comprises a body that is at least partially formed by mixing the matrix material and the hollow gas-filled beads to form a mixture, and curing the mixture.

6. The device of claim 1, wherein a diameter of at least a portion of the beads is from about 0.001 mm to about 3 mm.

7. The device of claim 1, wherein a diameter of at least a portion of the beads is about 1 mm or less.

8. The device of claim 1, further comprising an antenna for radiating or receiving an RF transmission.

9. The device of claim 8, wherein the composite material is proximal to the antenna or adjacent to the antenna.

10. The device of claim 1, wherein a weight percentage of the gas-filled beads is less than or equal to about 20% of composite material weight.

11. The device of claim 1, wherein a weight percentage of the gas-filled beads is less than or equal to about 15% of composite material weight.

12. The device of claim 1, wherein a weight percentage of the gas-filled beads is less than or equal to about 10% of composite material weight.

13. The device of claim 1, wherein a weight percentage of the gas-filled beads is less than or equal to about 5% of composite material weight.

14. A device suitable for implantation in a body of a host, the device comprising a composite material comprising a matrix material and a plurality of hollow gas-filled beads and further comprising an antenna for radiating or receiving an RF transmission, wherein the antenna is substantially encapsulated by the composite material, and wherein the composite material is configured to enhance tuning of the antenna.

15. The device of claim 14, wherein the composite material is proximal to the antenna or adjacent to the antenna.

16. The device of claim 14, wherein the beads are glass beads.

17. The device of claim 14, wherein the matrix material comprises a polymeric material.

18. The device of claim 17, wherein the polymeric material comprises an epoxy.

19. The device of claim 14, wherein the device comprises a body that is at least partially formed by mixing the matrix material and the hollow gas-filled beads to form a mixture, and curing the mixture.

20. The device of claim 14, wherein a diameter of at least a portion of the beads is from about 0.001 mm to about 3 mm.

21. The device of claim 14, wherein a diameter of at least a portion of the beads is about 1 mm or less.

22. A device suitable for implantation in a host, the device comprising electronics having an antenna for radiating or receiving an RF transmission and further comprising a body that substantially encapsulates the antenna, wherein the overall density of the device is about 1 $g/cm^3$, and wherein the body is formed of a composite material configured to enhance tuning of the antenna.

23. The device of claim 22, wherein the body is formed from a composite material comprising a matrix material and a plurality of hollow gas-filled beads.

24. The device of claim 23, wherein the composite material has an overall density of less than about 1 $g/cm^3$.

25. The device of claim 22, wherein the device is configured to measure glucose.

26. The device of claim 25, wherein the device is a wholly implantable glucose sensor configured for implantation in a subcutaneous tissue of a host.

* * * * *

UNITED STATES PATENT AND TRADEMARK OFFICE
CERTIFICATE OF CORRECTION

PATENT NO. : 7,637,868 B2 Page 1 of 1
APPLICATION NO. : 11/034343
DATED : December 29, 2009
INVENTOR(S) : Saint et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1198 days.

Signed and Sealed this

Ninth Day of November, 2010

David J. Kappos
*Director of the United States Patent and Trademark Office*